(12) United States Patent
Ataman-Onal et al.

(10) Patent No.: US 12,298,298 B2
(45) Date of Patent: May 13, 2025

(54) METHOD FOR DETECTING AN IMMUNE CELLULAR RESPONSE

(71) Applicant: BIOMÉRIEUX, Marcy l'Etoile (FR)

(72) Inventors: Yasemin Ataman-Onal, Reyrieux (FR); Michel Arnaud, Villeurbanne (FR); Franck Berthier, Saint Georges de Reneins (FR); Jacqueline Dupret-Carruel, Lyons (FR); Jacques Passagot, Saint Pierre la Palud (FR)

(73) Assignee: BIOMERIEUX, Marcy l'Etoile (FR)

( * ) Notice: Subject to any disclaimer, the term of this patent is extended or adjusted under 35 U.S.C. 154(b) by 956 days.

(21) Appl. No.: 16/611,180

(22) PCT Filed: May 4, 2018

(86) PCT No.: PCT/EP2018/061533
§ 371 (c)(1),
(2) Date: Nov. 5, 2019

(87) PCT Pub. No.: WO2018/202864
PCT Pub. Date: Nov. 8, 2018

(65) Prior Publication Data
US 2020/0191771 A1 Jun. 18, 2020

(30) Foreign Application Priority Data

May 5, 2017 (EP) ..................................... 17169653
Sep. 21, 2017 (EP) ..................................... 17192308

(51) Int. Cl.
*G01N 33/50* (2006.01)
*G01N 33/569* (2006.01)

(52) U.S. Cl.
CPC ....... *G01N 33/505* (2013.01); *G01N 33/5052* (2013.01); *G01N 33/5695* (2013.01)

(58) Field of Classification Search
CPC ............. G01N 33/505; G01N 33/5052; G01N 33/5695
See application file for complete search history.

(56) References Cited

U.S. PATENT DOCUMENTS

2004/0229368 A1* 11/2004 Rubio ....................... G01N 1/30
436/63
2015/0153361 A1 6/2015 Singh et al.

FOREIGN PATENT DOCUMENTS

| CN | 106053783 A | 10/2016 |
| EP | 1 144 447 B1 | 10/2009 |
| EP | 2 154 248 A1 | 2/2010 |
| EP | 2 417 456 B1 | 7/2016 |
| EP | 2 619 584 B1 | 10/2016 |

OTHER PUBLICATIONS

Neubauer et al. Towards standardized automated immunomonitoring: an automated ELISPOT assay for safe and parallelized functionality analysis of immune cells. Cytotechnology 69: 57-73 (Published online: Nov. 28, 2016).*
Boersma, Ykelien et al. "DARPins and other repeat protein scaffolds: advances in engineering and applications". Current Opinion in Biotechnology, vol. 22, pp. 849-857, 2011.
Klinman, Dennis et al. "ELISPOT Assay to Detect Cytokine-Secreting Murine and Human Cells". Current Protocols in Immunology, vol. 10, pp. 6.19.1-6.19.8, 1994.
Cox, Josephine et al. "Measurement of cytokine release at the single cell level using the ELISPOT assay". Methods, vol. 38, pp. 274-282, 2006.
Ellington, Andrew et al. "In vitro selection of RNA molecules that bind specific ligands". Nature, vol. 346, pp. 818-822, 1990.
Guisasola, M.C. et al. "Early inflammatory response in polytraumatized patients: Cytokines and heat shock proteins. A pilot study". Orthopaedics & Traumatology: Surgery and Research, vol. 101, pp. 607-611, 2015.
Gaur, Rajiv et al. "Impact of Blood vol. Tube Shaking, and Incubation Time on Reproducibility of QuantiFERON-TB Gold In-Tube Assay". Journal of Clinical Microbiology, vol. 51, pp. 3521-3526, 2013.
Kalyuzhny, Alexander. "Handbook of ELISPOT: Methods and Protocols". Methods in Molecular Biology, 2005.
Alvani, Ajit. "Diagnosing Tuberculosis Infection in the 21st Century: New Tools to Tackle an Old Enemy". Chest: Translating Basic Research Into Clinical Practice. vol. 131, pp. 1898-1906, 2007.
Neubauer, J.C. et al. "Towards standardized automated immunomonitoring: an automated ELISpot assay for safe and parallelized functionality analysis of immune cells". Cytotechnology, pp. 57-73, 2017.
Pai, Madhukar et al. "Gamma Interferon Release Assays for Detection of *Mycobacterium tuberculosis* Infection". Clinical Microbiology Reviews, vol. 27, pp. 3-20, 2014.
Rassaie et al., "Influence of different combinations of antibodies and penicillinase-labeled testosterone derivatives on sensitivity and specificity of immunoassays," Steroids, 1992, vol. 57, pp. 112-118.

(Continued)

*Primary Examiner* — Gailene Gabel
(74) *Attorney, Agent, or Firm* — Oliff PLC

(57) ABSTRACT

A method for detecting an immune cellular response including the steps of: (a) suctioning a defined amount of the sample by an automated suction/discharge device, (b) discharging this amount, using the device, into container R, containing, beforehand, at least one stimulant for secretion of the molecule by the at least one cell, or else not containing such a stimulant, (c) when the container does not contain the stimulant beforehand, introducing into container R the at least one secretion stimulant contained in container E, using the device, and (d) allowing the sample and stimulant to incubate, forming a mixture, by the at least one cell (i) in container R or (ii) in another container S after suctioning and discharge of the mixture using the device, and (e) detecting the immune cellular response, the detection of the immune cellular response indicates the presence of an immune cellular response specific for the stimulant.

18 Claims, 1 Drawing Sheet

(56) References Cited

OTHER PUBLICATIONS

Stabler et al., "Chemiluminescence Immunoassay of Aldosterone in Serum," Clinical Chemistry, 1991, vol. 37, No. 11, pp. 1987-1989.
Wood, P.R. et al. "Development of a simple, rapid in vitro cellular assay for bovine tuberculosis based on the production of γ interferon". Research in Veterinary Science, vol. 49, pp. 46-49, 1990.
Almeida, Coral-Ann et al. "Automation of the ELISpot assay for high-throughput detection of antigen-specific T-cell responses". Journal of Immunological Methods, vol. 344, pp. 1-8, 2009.
Janetzki, Sylvia. "Automation of the Elispot Technique: Past, Present, and Future". Journal of the Association for aboratory Automation, vol. 9, pp. 10-15, 2004.
Janetzki, Sylvia et al. "Guidelines for the automated evaluation of Elispot assays". Nature Protocols, vol. 10, pp. 1098-1115, 2015.
Bustin, S A. "Quantification of mRNA using real-time reverse transcription PCR (RT-PCR): trends and problems". Journal of Molecular Endrocrinology, vol. 29, pp. 23-39, 2002.
Giuletti, Annapaula et al. "An Overview of Real-Time Quantitative PCR: Applications to Quantify Cytokine Gene Expression". Methods, vol. 25, pp. 386-401, 2001.
Keller, George. "Non-Radioactive Labeling Procedures". DNA Probes, pp. 173-198, 1993.
Manak, Mark. "Radioactive Labeling Procedures". DNA Probes, pp. 137-172, 1993.
Kricka, Larry. "Nucleic Acid Detection Technologies—Labels, Strategies, and Formats". Clinical Chemistry, vol. 45, pp. 453-458, 1999.
Cavé, H. et al. "La RT-PCR en diagnostic clinique". Annales de Biologie Clinique, vol. 61, pp. 635-644, 2003.
Jemori, Takashi et al. "Investigation of the Molecular Mechanism of ICAN, a Novel Gene Amplification Method". J. Biochem, vol. 142, pp. 283-292, 2007.
Vincent, Myriam et al. "Helicase-dependent isothermal DNA amplification". EMBO Reports, vol. 5, pp. 795-800, 2004.
Jun. 12, 2018 Written Opinion of the International Searching Authority issued in International Patent Application No. PCT/EP2018/061533.
Jun. 12, 2018 International Search Report issued in International Patent Application No. PCT/EP2018/061533.
QuantiFERON®-TB Gold (Qft®) ELISA Package Insert, medical device by QIAGEN, Aug. 2016, www.QuantiFERON.com.
"eVol® XR Hand-Held Automated Analytical Syringe", Jun. 22, 2016, https://www.chromatographytoday.com/news/preparative/33/supelco/evolreg-xr-hand-held-automated-analytical-syringe/39260.
ThermoFisher Scientific web catalogue on "Electronic Pipettes", archived Nov. 18, 2016, https://web.archive.org/web/20161118041824/https://www.thermofisher.com/us/en/home/life-science/lab-plasticware-supplies/pipettes-pipette-tips/electronic-pipettes.html (with enlarged excerpt).
"Multipette®/Repeater® (X)stream—Operating Manual", Eppendorf, 2008.
McPherson et al. "Henry's Clinical Diagnosis and Management by Laboratory Methods" 23rd Edition, pp. 60-65 and 1191, Jun. 1, 2016, https://www.eu.elsevierhealth.com/henrys-clinical-diagnosis-and-management-by-laboratory-methods-9780323295680.html (with enlarged excerpt).
Fuhrmann, S. et al. "How Flow Cytometry is Changing the Study of TB Immunology and Clinical Diagnosis", Cytometry Part A, 73A, pp. 1100-1106, Aug. 2008.
Lynx, "Liquid Handling Robotic Workstation" brochure, Dynamic Devices, Jan. 25, 2017.
Dammermann, W. et al. "Development of a novel IGRA assay to test T cell responsiveness to HBV antigens in whole blood of chronic Hepatitis B patients", Journal of Translational Medicine, 13:157, 2015.
Schiller, I. et al. "Optimization of a Whole-Blood Gamma Interferon Assay for Detection of *Mycobacterium bovis*-Infected Cattle", Clinical and Vaccine Immunology, vol. 16, No. 8, pp. 1196-1202, Aug. 2009.
"MPA-10 / MPA-20 / MPA-200 / MPA-1200 / MPA-10000 Single Channel Electronic Pipette, MPB-200-8 MPB-1200-8 Multi Channel Electronic Pipette" Instruction Manual, Document WMPD4002874G, A&D Company Ltd., 2015.
"Cobas e 411 analyzer", Operator's Manual, Software Version 01-01, Roche Diagnostics, 2006.
Janeway, CA Jr. et al. "Immunobiology: The Immune System in Health and Disease", 5th Edition, Garland Science, Appendix I (7 pages), 2001.
"Quantikine@ HS ELISA, Human TNF-α Immunoassay", Catalog No. HSTAOOD, Instructions Version 12/13, R&D Systems, Inc., 2013.
Aug. 17, 2023 Notice of Further Oppositions issued for European Patent No. 3619533.

* cited by examiner

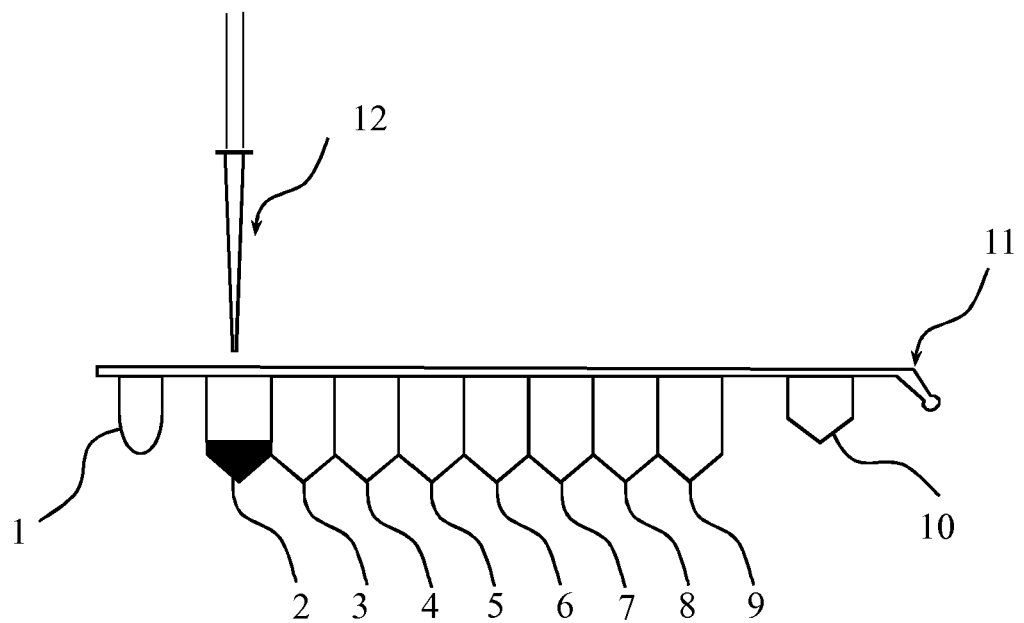

METHOD FOR DETECTING AN IMMUNE CELLULAR RESPONSE

BACKGROUND

The present invention relates to the field of the detection of immune cellular responses. In particular, the invention relates to a novel method for detecting an immune cellular response in a biological sample, said response being of use both in the diagnostic field and in the therapy field, in particular for toxicity studies on future medicaments and vaccines.

SUMMARY

The field of the detection of immune cellular responses is a field which has experienced a boom over the past few years. Thus, with the development of the ELIspot (enzyme-linked immunospot) test in the 1980s, originally used to measure immunoglobulin secretion by the B cells of a human organism, then broadened to all circulating blood cells capable of secreting a molecule after in vitro stimulation of said cells, even present in low amount, a broad medical field of application has opened up, in particular for gaining a better understanding and monitoring the immune response, for example in the context of infectious diseases or autoimmune diseases, and in the cancer field (Cox J. H. et al., 2006).

The immune response, brought about after the entry of an antigen into an organism, is of two types: it is either a humoral immune response, or a cell-mediated immune response. The humoral immune response, which comprises adaptive immunity with antibody production, is composed of four major steps: antigen recognition and clonal selection, clonal proliferation, differentiation of B lymphocytes into plasma cells which will secrete immunoglobulins (also called antibodies), thus forming immune complexes for neutralizing the antigen. This response makes it possible to act against extracellular microorganisms.

The cell-mediated immune response, also called cellular immune response or CMI (for Cell-Mediated Immunity) response, is adaptive immunity in which T lymphocytes (also called T cells) play a central role by activating the entire cascade of signals and responses in the face of an infection or an attack, such as, for example, the production of cytokines. The effector cells of cell-mediated immunity, such as cytotoxic T lymphocytes, make it possible to act against microorganisms. These two types of immune responses, "humoral" or "cell-mediated", use cells which secrete molecules, called immune effector molecules, namely the antibodies or cytokines, including chemokines.

The antigens which cause this immune response may be of infectious, exogenous origin, for example due to pathogens such as viruses, bacteria, fungi or parasites, or due to allergens, or else may be of endogenous origin, for example in the context of autoimmune diseases such as multiple sclerosis, type 1 diabetes, lupus, autoimmune thyroiditis, rheumatoid arthritis, ankylosing spondylitis, Goujerot-Sjögren syndrome, Crohn's disease, cancer diseases, etc.

Multiplication of a pathogenic agent within the organism, or release with pathogen-associated molecular pathogens ([PAMPs]), just like release of danger signals during a trauma, a burn or a surgical procedure, for example, are responsible for an immune and inflammatory reaction. This reaction comprises a humoral component and a cellular component. Furthermore, in all these situations, it combines a pro-inflammatory response (which is today considered to be responsible for the occurrence of organ failures and of early mortality), and also a compensatory anti-inflammatory response which, when it persists, is responsible for an immunosuppression phase, as is found in immunosuppressed patients, and which places patients at risk of secondary infections.

Besides these acute pathological conditions, other impairments of the immune balance are responsible for pathological conditions. Thus, chronic inflammatory diseases reveal an imbalance of the response in favor of excessive activation of the immune system, with a chronic destruction of the tissues affected, and the occurrence of a loss of function of the organ affected. Conversely, situations of innate immunosuppression (immune deficiency) or acquired immunosuppression (infection with the AIDS virus, chemotherapy, immunosuppression induced during organ transplantation, for example) reveal an insufficient response of the immune system with a risk of infection and of increased tumor formation.

The detection of the effector molecules produced by immune cells ex vivo makes it possible to improve the treatment of the patient, whether that is to assist in the diagnosis of these pathological conditions or to guide/personalize the therapeutic treatment.

The tests for detecting the cell-mediated immune (CMI) response can be used in various disciplines of immunology. For example, CMI assays make it possible to detect circulating T cells that react to the donor during organ transplantation; to measure the activity of the cytotoxic T lymphocytes for cancer research; to measure the memory responses for infectious diseases or vaccine development; and to detect autoreactive cells (which are typically at low frequency) in autoimmune diseases. The ELIspot test can also be used in the preclinical phase for determining whether a tested product could spark an adverse immune response, before using it on human beings.

The method for detecting the immune cellular response comprises two phases:

1) Phase 1—Secretion: Incubation of the cells of interest from a biological sample containing them and capable of secreting the molecule to be detected, under conditions allowing secretion of the molecule. For this step, the terms "cell culture" or "stimulation" can then be used. The cells are cultured in a liquid medium, it being possible for this liquid medium to be either a biological fluid (the one from the sample), which is pure or diluted in a buffer, or a culture medium, or a mixture of the two. This secretion is obtained in the presence of a stimulant, this stimulant possibly being specific, as in the case of immune responses directed against an infectious agent, or possibly being nonspecific, such as, for example, in the case of cellular immune responses due to an immune deficiency.

2) Phase 2—Detection of the immune cellular response: it can be carried out by detection or quantification of the molecule secreted at the end of phase 1 (the term "analyte" is then used instead) by carrying out an assay of the secreted molecule, by any type of technique suitable for detecting secreted molecules, such as by immunoassay, for example of ELISA (Enzyme-Linked Immunosorbent Assay), RIA, chemoluminescence or ELFA (Enzyme-Linked Fluorescent Assay) type, by bioassay, or by a biochemical technique, by a proliferation assay, by a molecular biology test or by flow cytometry.

An example of an infectious pathological condition in which the diagnosis takes into account the detection of the immune cell response due to cells of the infected organisms is tuberculosis. For several decades, the only available test was the skin test. Said test makes it possible to determine whether the individual tested has been in contact with the *Mycobacterium tuberculosis bacillus*. To do this, the physician performs an intradermal reaction in order to bring the individual's immune cells into contact with a preparation of tuberculin. The latter causes an inflammatory response (skin reaction) in patients who have been in contact with the *Mycobacterium tuberculosis bacillus* (presence of redness at the injection). However, carrying out the technique is complex and reading the result is subjective and requires that the healthcare provider has expertise. Furthermore, this test does not make it possible to quantify the cytokines secreted.

There are two commercial blood tests which show whether patients have been in contact with the *Mycobacterium tuberculosis bacillus* by measuring, in vitro, the release of interferon gamma (IFN-γ) by the cells in response to stimulants which are antigens that are highly specific for *Mycobacterium tuberculosis*. These stimulated antigens are in particular at least ESAT6 and CFP10 and are absent from the BCG (Bacillus Calmette-Guérin) vaccine and from most nontuberculous mycobacteria (Lalvani, A., 2007). These assays are called IGRA assays (for Interferon Gamma Release Assay).

The first test is the T-SPOT®.TB test from Oxford Immunotec [Oxford, Great Britain], an ELISpot blood assay which measures the release of cytokine from isolated cells. For this test, the blood sample is first of all taken in a laboratory in a heparinized sterile tube, for example a Vacutainer® tube (Becton-Dickinson) or a Greiner, Terumo, Sarstedt, etc., tube.

The PBMC cells (peripheral blood mononuclear cells) are then separated from the total blood by several steps of centrifugation on a Ficoll density gradient, washed and counted. For each blood sample, the PBMCs which are derived therefrom are cultured in a microtitration plate (also called microplate) under three different conditions: (i) in the presence of the specific stimulating antigens (for example ESAT-6, CFP-10), (ii) in the presence of one or more nonspecific mitogens (positive control) and (iii) in the presence of the stimulation medium only (negative control). The microplates thus prepared are incubated under conditions which allow the secretion of IFN-γ, for example at 37° C., 5% $CO_2$ in a cell culture incubator for 16 to 20 hours. This step of introduction of the secretory cells and of cell culture is carried out under a laminar flow host in order to maintain sterile conditions during the cell culture. The final step consists in detecting the cytokine thus secreted by means of an anti-IFN-γ capture antibody previously applied to the bottom of the microtitration plate, of a detection partner which binds to the cytokine and of a substrate, thus forming countable spots on the membrane, each spot corresponding to a secretory cell. The principle of such an ELIspot assay is described for example in the book Handbook of Elispot, 2005, and in particular on page 17. This test has the drawback that it is manual, that it requires prior purification (separation) of the PBMCs from the total blood using one or more centrifugation steps, and also the use of a particular device (laminar flow hood) in order to guarantee sterility for transferring the blood sample into the plate and during the cell culture. Furthermore, this test is a highly technical complex test requiring well-trained technical staff.

The second test is the QuantiFERON®-TB Gold test [Qiagen] which measures the total concentration of IFN-γ released by all the cells in the supernatant of a blood sample, by ELISA. In this test, the blood sample must be taken from the patient directly into three specific sterile blood sample tubes, one containing the stimulating antigens (ESAT-6, CFP-10 and TB7.7), another containing a mitogen (positive control) and the final tube being the "NIL" tube (negative control). Then the tubes, still sterile, are incubated at 37° C. for 16 to 24 hours in order to allow secretion of the interferon gamma, so that the simulation step takes place under sterile conditions. The tubes are then centrifuged, and the plasma is removed and placed, by means of a pipette, in a microplate containing an anti-IFN-γ capture antibody. The amount of IFN-γ is then measured by ELISA by means of a revealing partner and of an enzymatic substrate. This test has several drawbacks. First of all, this test is not automated. It requires centrifugation, like the T-SPOT® test, so that it cannot be easily automated. Furthermore, since the blood sample tubes used already contain the stimulating antigens, the interferon-gamma-secreting cells are immediately brought into contact with these stimulating antigens, leading to particular and restrictive handling up until the IFN-γ assay. Indeed, it is necessary to place these tubes at ambient temperature (22+/−5° C.) in order to slow down the secretion, and to carry out the IFN-γ assay within a given period of time starting from the moment the blood is brought into contact with the stimulants (maximum 16 h). This is also detrimental to the reproducibility of the results: depending on the organization constraints of laboratories, the time between the collecting of the sample and the stimulation at 37° C. for the secretion can vary greatly. Finally, as indicated above, this test uses particular sterile sample tubes, which not only contain beforehand the stimulating antigens, but which are different depending on the altitude at which the assays are carried out (different tube references), which is more difficult from a stock management point of view for a laboratory compared with the use of conventional sterile tubes, such as for the T-SPOT® test.

Of course, tuberculosis is not the only pathological condition for which cell tests are used, as previously emphasized. In addition, these tests are also used for other mammals (Wood P. R., 1990).

However, regardless of the test, a major drawback, in addition to the automation difficulty because of the need for a centrifugation step, is linked to the lack of reproducibility (Pal M. et al., 2004). This lack of reproducibility is explained by several factors, an important one of which relates to the sample volume which may be different from one blood sample to the other. This results in a decrease in the sensitivity of the tests (Gaur R L, et al., 2013). The sample volume fluctuation is due to the taking of the blood sample carried out, by virtue of the tubes used, which are under vacuum, with a depression calculated for sampling approximately 1 ml of blood, that is to say between 0.8 and 1.2 ml. Thus, the ratio of stimulating antigens of the specific tube/blood volume is different from one sample to another, which necessarily has an impact on the amount of cytokine secreted and therefore on the reproducibility of the measurement thereof. Being able to have a system that would always take exactly the same amount of sample would make it possible to overcome this drawback.

Almeida C A. M. et al., 2009 propose an automated ELIspot test after purification of the PBMCs by centrifugation, which comprises counting the cells and counting the spots. To do this, they use robotics for sample and reagent manipulation and an integrated information system for electronically monitoring the performance of the assay. This test is in fact only partially automated since the automation does not include in particular the preparation of the PBMCs and the introduction of the stimulating peptides into the 96-well plates. Furthermore, this test includes particular steps, either before the automation, such as a sample centrifugation step for separating the cells, which is difficult to automate, or during the automation, such as a cell counting step.

Neubauer J. C. et al., 2017 propose a more automated ELIspot test after the PBMC purification by centrifugation, which goes from the counting of the cells to the counting of the spots, via cell culture (stimulation for the secretion by the cells). It involves the use of a pipetting robot of Tecan type, in order to automate the steps for dispensing the cells, the various reagents and the washing solutions. However, this solution requires at least two particular and expensive pieces of equipment, which would make mass production complicated. Indeed, this automation requires in particular the use of a laminar flow hood over the entire automation device in order to adhere to sterility during the cell culture, a required condition which forms the basis of cell culture (Coligan J. E., 1994). Finally, as with the test of Almeida C A. M. et al., 2009, particular steps are required, (i) either before this automation, such as a sample centrifugation step for separating the cells, which is, as previously indicated, difficult to automate, (ii) or during the automation, such as a cell counting step.

The applicant has found, against all expectations, that it is possible to overcome the drawbacks of the prior art processes and to carry out the detection of the immune cellular response by automating the step of cell stimulation which is carried out directly in the biological sample to be tested which is as taken, and thus nonmodified after sampling, without recourse either to a centrifugation step, or to a cell separation step, or to a cell-counting step, thereby making it possible to greatly simplify the automated instruments to be used for such an automated detection.

Thus, the invention relates to a method for detecting an immune cellular response in a biological sample of animal origin, which may contain at least one cell which secretes at least one immune effector molecule, comprising the steps consisting in:
(a) suctioning a defined amount of the biological sample as taken by means of an automated suction/discharge device,
(b) discharging this defined amount, using said automated suction/discharge device, into a container R, said container R containing, beforehand, at least one stimulant for secretion of said molecule by said at least one cell, or else said container R not containing such an at least one stimulant,
(c) when the container does not contain, beforehand, at least one secretion stimulant, introducing into said container R said at least one secretion stimulant contained in a container E, using said automated suction/discharge device, and
(d) leaving the defined amount of sample and said at least one stimulant to incubate, forming a mixture, for the secretion of said molecules by said at least one cell (i) in said container R or (ii) in another container S after suctioning and discharge of said mixture using said automated suction/discharge device, and
(e) detecting the immune cellular response, in which the detection of the immune cellular response indicates the presence of an immune cellular response specific to said at least one secretion stimulant.

As indicated above, the method for detecting the immune cellular response of the invention can be divided into two phases: a phase of stimulating the cells which secrete or are capable of secreting at least one immune effector molecule, contained in a biological sample of animal origin, for the secretion of said molecule (steps (a) to (d)) and a phase of detecting said response after stimulation (step (e)). Thus, the invention also relates to the first phase, namely an automated method for stimulating at least one cell capable of secreting an immune effector molecule for the secretion of said molecule, said at least one cell being from a biological sample of animal origin, characterized in that it comprises or consists of the steps consisting in:
(a) suctioning a defined amount of the biological sample as taken by means of an automated suction/discharge device,
(b) discharging this defined amount, using said automated suction/discharge device, into a container R, said container R containing, beforehand, at least one stimulant for secretion of said molecule by said at least one cell, or else said container R not containing such an at least one stimulant,
(c) when the container does not contain, beforehand, at least one secretion stimulant, introducing into said container R said at least one secretion stimulant contained in a container E, using said automated suction/discharge device, and
(d) allowing the defined amount of sample and said at least one stimulant to incubate, forming a mixture, for the secretion of said molecule by said at least one cell (i) in said container R or (ii) in another container S after suctioning and discharge of said mixture using said automated suction/discharge device.

The immune cellular response thus obtained is particularly useful in various medical applications. Thus, the invention also relates to the use of the method for detecting the immune cellular response of the invention or of the automatic stimulation method of the invention, for the diagnosis of pathological conditions, for medicament and vaccine toxicity studies and for determining the immune status of a patient.

The applicant has thus found, against all expectations, that it was possible to greatly improve the detection of the immune cellular response in a biological sample of animal origin that may contain at least one cell which secretes at least one immune effector molecule by automating the step of cell stimulation directly in the biological sample to be tested, having never been modified after taking the sample, for instance having never been subjected to either a centrifugation step, in particular for separating the cells before or after stimulation, or a step of counting the cells as in the context of an ELIspot assay and having never been brought into contact with a stimulation stimulant. This provides many advantages including, inter alia, the use of a simple automated instrument, the use of standard tubes for taking the biological sample, that is to say not containing beforehand any stimulant and suitable for any implementation condition, such as tubes containing lithium heparinate, better control of the total time between bringing together the sample and the stimulant(s) and detecting the immune cellular response, and also control of the sample volume for the cell stimulation.

BRIEF DESCRIPTION OF THE DRAWING

FIG. 1 is a schematic representation of a tip belonging to an automated suction/discharge device according to the disclosed embodiments, and a strip used with the suction/discharge device.

DETAILED DESCRIPTION

The term "immune cellular response" is intended to mean both the cell-mediated immune response and the humoral immune response generated after stimulation of the cells which secrete or are capable of secreting an immune effector molecule with at least one secretion stimulant, which cells are contained in a biological sample.

The cells contained in the biological sample and capable of secreting at least one immune effector molecule comprise the effector cells of cell-mediated immunity, for example lymphocytes such as Natural Killer (NK) cells and T cells (CD4+ and/or CD8+), which will secrete one or more cytokines, the effector cells of humoral immunity, for example B cells, which will secrete antibodies, macrophages and monocytes, and also dendritic cells, which will secrete cytokines or chemokines. As indicated above, these immune cells are capable of secreting the molecules of interest in the presence of one or more secretion stimulants.

The term "secretion stimulant" is intended to mean any element which leads to the secretion by the cell, brought into contact with this stimulant, of an immune effector molecule which is a protein such as a cytokine, antibody or marker, or an RNA transcript of the gene of the immune effector molecule. The term "RNA transcript" is intended to mean RNAs, and in particular messenger RNAs, resulting from the transcription of the gene of the immune effector molecule. According to the immune response that it is desired to obtain, linked to the pathological state in question, which is itself possibly linked to a pathogenic microorganism, the stimulant will be specific for the pathogenic microorganism or nonspecific, which constitutes one particular embodiment of the invention. As opposed to the stimulant specific for a pathogen, it will be possible to use without distinction for all the other stimulants which are nonspecific, either a nonspecific stimulant, or a stimulant nonspecific for a pathogen.

Thus, for all the pathological states not linked to a pathogenic microorganism, such as for example autoimmune diseases, for example multiple sclerosis, type 1 diabetes, lupus, autoimmune thyroiditis, rheumatoid arthritis, ankylosing spondylitis, Goujerot-Sjögren syndrome, Crohn's disease), traumas, including serious traumas comprising polytrauma lesions, such as a wound, fracture, burn, etc., grafts, the method of the invention can use one or more nonspecific stimulants, also called mitogens, such as protein kinase A (PKA), phorbol myristate acetate (PMA), phytohemaglutin (PHA), concanavalin A (conA), Pokeweed mitogen (PWM), Staphylococcal Enterotoxin B (SEB) and lipopolysaccharide (LPS).

For the pathological states linked to a pathogenic microorganism, for example the pathological states linked to a virus, such as acquired immune deficiency syndrome (HIV, SIV, FIV virus), hepatitis (HCV, HBV, HAV, HEV virus), chickenpox (VZV virus), infections linked to the cytomegalovirus (CMV), infectious mononucleosis (EBV virus), the various herpes-type infections (HSV1, HSV2 virus), pathological states linked to bacteria, such as tuberculosis (*Mycobacterium tuberculosis, Mycobacterium bovis, Mycobacterium leprae*), Lyme disease (*Borreliosis Borrelia burgdorferi stricto sensu, Borrelia afzelii, Borrelia garinii, Borrelia spielmanii*), infections linked to clostridia (for example *Clostridium difficile, Clostridium botulinum*), salmonellosis, pneumonias and other pathological conditions of the respiratory apparatus (for example *Klebsiella, Leugionella*), urinary diseases (*Proteus, Klebsiella*), intestinal infections (for example *Escherichia coli, Shigella*), nosocomial infections (for example *Pseudomonas aeruginosa, Staphylococcus aureus*) or Syphilis (*Treponema pallidum*), pathological states linked to yeasts, such as candidiasis (*Candida albicans*), fungal infections such as aspergillosis (*Aspergillus fumigatus*) and mucormycosis (Mucorales), pathological conditions linked to a parasite, such as malaria (*Plasmodium falciparum, Plasmodium vivax, Plasmodium ovale, Plasmodium malariae, Plasmodium knowlesi*), schistosomiasis (*Schistosomia mansoni, Schistosomia japonicum*), the stimulant will be pathogen-specific. It will comprise at least one pathogen-specific antigen leading to the production by the cells from the biological sample either of a cytokine, or of an antibody directed against this antigen, depending on the nature of the cells stimulated.

Examples of pathogen-specific stimulants comprise peptide molecules (proteins or parts of proteins) which can originate from the pathogen, for example from the envelope in the context of a virus, or they can be secreted by the pathogen itself. These molecules can be used whole or in the form of peptide fragments of variable length, for example at least 7, 8, 9, 10, 11, 12, 13, 14, 15, 16, 17, 18, 19 or 20 amino acids and of at most the whole protein, or of at most 30, 35, 40, 41, 42, 43, 44, 45, 46, 47, 48, 49 or 60 amino acids. The method of the invention may use one or more peptide stimulants, of equal or different amino acid length. For example, it may use at least one peptide stimulant having a length of between 7 and 15 amino acids and at least another peptide stimulant of at least 16 amino acids and at most the whole protein. The method of the invention may use one or more stimulants originating from different pathogen strains.

When a vaccine exists, it may be that the specific stimulants used are not those present in the vaccine so as to subsequently allow a use of the method of the invention in diagnostic applications, for example for verifying in the vaccinated patient whether said patient has been in contact with the pathogen. The composition of vaccines is known so that it is easy for those skilled in the art to choose the appropriate pathogen-specific antigenic stimulants.

Pathogen-specific stimulants are well known to those skilled in the art. By way of nonlimiting examples, mention may be made of the PPD (Protein Purified Derivate) stimulant, the ESAT-6, CFP-10, TB7.7, TB37.6, Rv3615c proteins or fragments thereof for the *Mycobacterium tuberculosis* pathogen (EP2154248A, EP1144447A, EP2417456A), the pp28, pp50, pp65, IE-1, IE-2, gB proteins or fragments thereof for the Cytomegalovirus pathogen and the peptides of the Epstein-Barr virus (EBV) of Pep Tivator® type provided by the company Miltenyi Biotec. Mention may also be made of the cells of *Borrelia*, for example heat-inactivated, which may comprise several strains of *Borrelia*, such as *Borrelia burgdorferi, Borrelia garinii* and *Borrelia afzelii* (EP2619584A).

According to one embodiment, the method of the invention is such that it uses at least one specific stimulant which is an antigen highly specific for *Mycobacterium tuberculosis*, which may be absent from the BCG (Bacillus Calmette-Guérin) vaccine. Preferably, said at least one specific stimulant is chosen from the ESAT-6, CFP-10 and TB7.7 antigens.

The cytokines are any known cytokines secreted by immune cells such as T cells, for instance interferon gamma (IFN-γ), interleukins (ILs), such as IL-2, IL-4, IL-6, IL-10, IL-12, IL-13, IL-16, IL-17, IL-la, IL-1p, IL-1ra (IL1RN), chemokines such as the CC chemokines, the C chemokines, the CXC chemokines and the CX3C chemokines, tumor necrosis factor α (TNFα), colony stimulating factor (CSF), such as granulocyte colony stimulating factor (G)-CSF or granulocyte macrophage colony stimulating factor (GM)-CSF, and also complement or components of the complement biological pathway, for example C5a, Groα (CXCL1), sICAM-1 (CD54), IP-10 (CXCL10), I-TAC (CXCL11), MCP-1 (CCL2), MIF (GIF), MIP-la (CCL3), MIP-1β (CCL4), RANTES (CCL5) and MIG (CXCL9).

According to one embodiment, the cells to be stimulated are cells capable of secreting at least one cytokine.

According to another embodiment, said at least one cytokine that it is desired to have secreted is chosen from interleukins, chemokines, tumoral necrosis factor α (TNFα) and interferon gamma (IFNγ), interferon gamma being a cytokine of choice.

In addition to cytokines, the cells to be cultured according to the automated method of the invention may also be capable of secreting at least one antibody.

Thus, according to one particular embodiment, the cells cultured are B cells capable of secreting at least one antibody in the presence of at least one nonspecific stimulant or of at least one stimulant specific for a pathogenic microorganism.

The nonspecific stimulants or stimulants specific for a pathogenic microorganism which bring about the production of antibodies are known to those skilled in the art, and examples comprise those described above for T cells. Other examples comprise the surface antigens of the various pathogens, such as the HBs antigen for hepatitis B virus, the flu virus surface antigen, and also the proteins of an individual which generate autoantibodies in said individual. In general, regardless of the stimulant, said stimulant will be the antigen specific for the antibody response obtained. Thus, the antibody that will be secreted will be an antibody directed against this antigenic stimulants.

The biological samples containing the cells capable of secreting the immune effector molecule(s) suitable for the purposes of the invention are any sample containing such cells, such as biological fluids, for example total blood and derivatives thereof, cerebrospinal fluid, synovial fluid, lachrymal fluid, gingival fluid, urine and saliva. Preferably, the biological sample is a sample of total blood and derivatives thereof.

The biological samples are not modified before their use in the method of the invention, that is to say that they are used as they are following the taking of the sample from the animal organism and that they are not brought into contact beforehand with at least one stimulant. Thus, the sample is taken into a container, for example a vial, not containing stimulant. Likewise, and as indicated above, the biological samples also are not subjected to a cell separation or cell counting step. The term "crude sample" or "sample as taken" or "sample of origin" can then be used, this sample being not previously brought into contact with at least one stimulant.

The animal organisms from which the biological samples come are the beings for whom a medical diagnosis is usually carried out or to whom medicaments are given. They comprise for example mammals, such as human beings, bovines, members of the canine family, members of the feline family, members of the equine family, members of the sheep family, members of the goat family, members of the porcine family, rabbits, reptiles, amphibians, and also birds such as gallinaceous birds, or birds of prey.

According to one embodiment, the biological sample is a sample of human, bovine, canine, feline or equine origin, preferably human origin.

The first step of the detection or quantification method of the invention comprises the suctioning of a defined amount of the biological sample as taken by means of an automated suction/discharge device (step (a)).

The term "defined amount" is intended to mean an amount or a volume of sample that is calibrated and always identical from one assay to another owing to the use of an automated suction/discharge device.

The automated suction/discharge devices are devices widely known to those skilled in the art and are present in a large number of biochemistry, molecular biology and immunoassay instruments, for example the instruments of the VIDAS® range, such as VIDAS®, miniVIDAS®, VIDAS® 3 (bioMérieux), Simoa® HD-1 (Quanterix), Cobas® or Elecsys® (Roche Diagnostic Gmbh), LIAISON® (Diasorin), Architect® (Abbott), Access (Beckman Coulter), Clarity™ (Singulex®), Vitros® (Johnson & Johnson), Centaur® (Siemens), eMAG® and easyMAG® (bioMérieux). These automated suction/discharge devices comprise one or more sampling devices for suctioning a liquid medium, such as the biological sample or the reaction media, from the container which contains it, then subsequently for discharging it. They comprise for example an arm or a support at the end of which is inserted a needle or an endpiece (tip), which endpiece is uncoated or previously coated with binding partners, such as for example SPR® from the VIDAS® range.

Since the sampling device is used to suction then to discharge various media, first of all the biological sample, then various reaction media, the endpieces of said suction/discharge device can be changed and discarded into a bin at various times in the method. Thus, for example, in the context of the VIDAS® instrument, a first endpiece is used to take the biological sample, then, if necessary, another endpiece is used to provide said at least one secretion stimulant, then another endpiece coated with binding partner (SPR®) is used to measure the cellular response. When the suction/discharge device comprises several sampling devices, each sampling device has its own role. For example, a first sampling device can serve to suction/discharge the biological sample and a second sampling device can serve to suction/discharge the reagents required for example for the incubation and for the measurement of the cellular response. The sampling device is guided by a suction/discharge control device, such as for example a device which brings about a pressure difference in the sampling device by means of a piston driven by any means known to those skilled in the art, such as for example by means of a screw coupled to a motor, forming a pump unit, it being possible for the sampling device and the suction/discharge control device to be connected by means of tubing comprising seals in order to guarantee leaktightness. The sampling device and the suction/discharge control device may be at varying distances from one another. Those skilled in the art will adjust the suction rate and power of the suction/discharge control device as a function of the amount of sample that it is desired to take with a view to the stimulation and, where appropriate, as a function of the length and cross section of the tubing between the suction/discharge control device and the sample container. Thus, for example, in the context of the VIDAS® 3 instrument wherein the pump unit is close to the tip, the suction rate will be between 10 and 500 µl/second.

The sample container is any container suitable for receiving a sample: tube, vial. It may be made of plastic, such as of ethylene vinyl acetate (EVA copolymer), polyethylene, polypropylene copolymer, fluorinated ethylene propylene (nalgene), made of glass or made of stainless steel. In the case of blood or derivative, the sample container may be a vacuum-type blood sampling tube, for example a Vacutainer®, Greiner or Terumo tube, for example a heparinized tube, conventionally used for taking blood from a patient.

The sample container or its content will be placed in the instrument carrying out the automated method of the invention before this method is carried out, for example by an operator or by another automated device.

The amount/volume of biological sample that will be suctioned by said automated suction/discharge device will be easily defined by those skilled in the art as a function of several parameters, such as the instrument that is going to be used and the nature of the biological sample. In general, the amount of biological sample that will be suctioned from the sample container will be between 5 and 800 µl, preferably between 10 and 500 µl. This amount will be at least 10, 15, 20, 25, 30, 35 or 40 µl and at most 100, 150, 200, 250, 300, 350 or 400 µl.

Once the calibrated defined amount of biological sample has been suctioned, it is then discharged by the same suction/discharge device into a container called container R in which the actual stimulation (incubation) will be able to take place.

As for the sample container, the container R may be made of plastic, such as of ethylene vinyl acetate (EVA copolymer), polyethylene, polypropylene copolymer, fluorinated ethylene propylene (nalgene), made of glass or made of stainless steel.

The container R may contain beforehand all the components required for the stimulation, for example, where appropriate, said at least one secretion stimulant, and also one or more buffers, such as phosphate, borate, Tris, HEPES buffers, or else it may contain only some of the components, for example, where appropriate, said at least one secretion stimulant, in particular in freeze-dried form (as powder, microbeads, capsules, etc.), the other components, present in another container, being brought into the container R by the suction/discharge device after discharge of the defined amount of biological sample for carrying out the incubation step. Alternatively, the container R may be empty, with the components required for the integration, present in another container, being brought into the container R by the suction/discharge device after discharge of the defined amount of biological sample for carrying out the incubation step. In particular, said at least one secretion stimulant may be contained in a container E and is introduced into the container R by the suction/discharge device after discharge of the defined amount of biological sample (step (c)). Said at least one secretion stimulant is contained in the container E either in freeze-dried form, or as a mixture with one or more buffers, as described above. According to one embodiment, the container R does not contain said at least one secretion stimulant, which is contained in a container E.

This container R or E may consist of a single unit element, for example a vial, a tube, a dish or a well, or else it may be included in a set of several containers, such as for example a microtitration plate or a strip containing several wells, such as the strips sold for use in the VIDAS® instrument (bioMérieux, France). In the latter case, the containers R and E may be in the same plate or the same strip.

The container R may or may not be sterile before the introduction of the defined amount of biological sample. In any event, it is clean, that is to say that it contains a very low amount of microorganisms. The container R may be covered with a sealing element that will be pierced for the introduction of the defined amount of sample. For example, the container R will be pierced by the suction/discharge device during the discharge step. This also applies to the container E. The sealing element is for example an aluminum foil, a polymer film, a septum or an adhesively bonded plastic sheet. The opening of the sealing element may vary from partially to totally, that is to say that the stimulation container R may be entirely open or open only over the diameter of the suction/discharge device.

For example, if the sampling device contains a pipette tip, which has a conical shape at its end, the suction/discharge device will be programmed by its suction/discharge control device so that the sealing element is pierced only by the part comprising the smallest diameter of the tip. Thus, the sealing element may be pierced over a diameter of between 0.5 mm and 5 mm.

The incubation of the defined amount of sample and of said at least one stimulant, forming a sample-stimulant mixture, also called stimulation step, can be carried out at a temperature which is normally that of the cells in vivo, namely a temperature close to the average central temperature of the animal organism from which the biological sample is derived, which constitutes one particular embodiment of the invention. Indeed, each organism has their own average central temperature. Thus, the average central temperature for a human being is 37° C., that of bovines is 38.6° C., that of dogs is 38.9° C., that of cats is 38.6° C., that of horses is 37.8° C., that of rabbits is 39.5° C. and that of chickens is 41.7° C. For cold-blooded vertebrates, the average central temperature is between 18° and 25° C. Thus, according to whether the biological sample comes from one animal organism or another, the temperature to be used in the incubation step of the method of the invention may be different and those skilled in the art will choose the correct temperature as a function of the biological sample used and of the corresponding average central temperature. Since the cells are capable of withstanding a variation, the incubation temperature in the method of the invention will preferably be that of the central temperature of the animal organism from which the biological sample is derived + or −3° C., preferably + or −2° C., or + or −1° C. For example, for human beings, the cells will be stimulated between 34 and 40° C., preferably between 35 and 39° C. or else between 36 and 38° C., or else at 37° C. In general, the incubation temperature will be between and 45° C., preferably between 35° C. and 43° C. According to one embodiment, the temperature of the incubation step will be at least 19, 20, 21, 22, 23, 24, 25, 26, 27, 28, 29, 30, 31, 32, 33, 34 or 35° C. The temperature may be at most 38, 39, 40, 41, 42, 43 or 44° C.

The duration of the incubation step can vary, in particular as a function of the amount of cells present in the biological sample, and is generally between 1 h and 72 h. According to one embodiment, the duration of the incubation step is at least 2, 3, 4, 5, 6, 7, 8, 9, 10, 11, 12, 13, 14, 15, 16, 17 and 18 h and it is at most 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 51, 54, 57, 60, 63, 66, 69, 70 or 71 h. Preferably, the duration of the incubation step is between 2 and 24 h, and more preferably between 6 and 18 h.

The incubation may be carried out (i) in said container R, which is preferred, or else (ii) in another container S after suctioning and discharge of said mixture using said automated suction/discharge device.

It is conventionally known practice to carry out the step of incubating the immune cells, contained in the biological sample or separated, as in Elispot, with the secretion stimulant(s) under sterile conditions. However, the applicant has shown that this condition is not necessary. Thus, the container R does not need to be placed under sterile conditions during the cell incubation step. Thus, according to one embodiment, the container R is non-sterile after introduction of the defined amount of sample and/or the incubation step (d) is carried out under non-sterile conditions, which is entirely unexpected.

While the implementation of an incubation step under sterile conditions requires a particular device for adhering to these conditions, such as a laminar flow hood or a vacuum blood sampling tube, the implementation of an incubation step under non-sterile conditions is particularly easy insofar as it requires no particular device. Thus, any biochemistry, molecular biology or immunoassay instrument comprising an automated suction/discharge device as described above is suitable for such an incubation step under non-sterile conditions.

The final step of the method of the invention consists in detecting the immune cellular response which is specific for said at least one secretion stimulant, directly from the sample-stimulate mixture since, against all expectations, no centrifugation of the cells is necessary before the detection of this immune cellular response. The expression "specific for said at least one secretion stimulant" is intended to mean that the use of another stimulant with the same type of cell (B or T) could give a different response, for example other antibodies or other cytokines.

The detection of the immune cellular response can be carried out by any method known to those skilled in the art, such as by immunoassay, by proliferation assay, by measurement of the expression level of the RNA transcripts according to methods known in molecular biology or by flow cytometry. It may or may not use at least one partner for binding to the immune effector molecule or to its corresponding RNA transcript, which comprises any partner capable of binding to said molecule or to said transcript. The nature of the binding partner will depend on the nature of the analyte and on the type of assay carried out. Preferably, the test will be an immunoassay or a molecular biology test.

Of course, the term "immuno" in "immunoassay" for example is not considered in the present application to strictly indicate that the binding partner is an immunological partner, such as an antibody. This is because those skilled in the art also widely use this term when the binding partner, also called ligand, is not an immunological partner but is, for example, a receptor for the analyte that it is desired to assay. Thus, it is known practice to refer to the ELISA assay ("Enzyme-Linked Immunosorbent Assay") for assays which use non-immunological binding partners, more widely called "Ligand Binding Assay", although the term "immuno" is included in the acronym ELISA. In the interests of clarity, throughout the application, the applicant will use the term "immuno" for any test or assay using a binding partner, even when it is not an immunological partner.

If step (e) uses at least one partner for binding to the immune effector molecule, it can comprise the steps consisting in:
(e') bringing said secreted immune effector molecule into contact with at least one partner for binding to said molecule and
(f') revealing the presence or the amount of molecule by virtue of its binding to said at least one binding partner.

By way of examples of an immunoassay binding partner, mention may be made of binding partners of immunological nature or origin, such as antibodies (monoclonal or polyclonal) and antibody fragments (such as Fab, Fab', F(ab')2), scFv chains (single chain variable fragments), dsFv chains (double-stranded variable fragments)), well known to those skilled in the art, and also binding partners which are not of immunological nature or origin, such as proteins other than antibodies, peptides, oligonucleotides, nanofitins, receptors for the molecule of interest if they exist, aptamers, DARPins or any other molecule which is known to have an interaction with said molecule of interest.

Nanofitins (trade name) are small proteins which, like antibodies, are capable of binding to a biological target, thus making it possible to detect it, to capture it or quite simply to target it within an organism.

Aptamers are oligonucleotides, generally RNA or DNA, identified in libraries containing up to $10^{15}$ different sequences, by a combinatorial in vitro selection method called SELEX for "Systematic Evolution of Ligands by Exponential Enrichment" (Ellington A D and Szostak J W., 1990). Most aptamers are RNA compounds, because of the capacity of RNA to adopt varied and complex structures, which makes it possible to create, at its surface, cavities of varied geometries, making it possible to bind various ligands. These are biochemical tools of interest which can be used in biotechnological, diagnostic or therapeutic applications. Their selectivity and their ligand-binding properties are comparable to those of antibodies.

"DARPins" for Designed Ankyrin Repeat ProteINS (Boersma Y L and Plütckthun A, 2001) are another class of proteins which make it possible to mimic antibodies and to be able to bind, with high affinity and high selectivity, to target proteins. They derive from the family of ankyrin proteins which are adapter proteins that make it possible to bind membrane proteins integral to the spectrin/actin network which constitutes "the vertebral column" of the cell plasma membrane. The structure of ankyrins is based on the repetition of a motif of approximately 33 amino acids and the same is true of DARPins. Each motif has a secondary structure of helix-turn-helix type. DARPins contain at least three, preferably four to five, repeat motifs and are obtained by screening of combinatorial libraries.

Examples of binding partners comprise anti-IFN-γ antibodies, anti-antibody antibodies, pathogen proteins or fragments thereof (for example the NS3 protein of HCV, the HBsAg protein of HBV, etc.) and phage proteins, which are widely known to those skilled in the art and commercially available.

The bringing of the secreted immune effector molecule into contact with said at least one binding partner is carried out in a container other than the container R or in the container R. In the latter case, the binding partner is contained beforehand in the container R or else it will subsequently be introduced therein by the suction/discharge device. If the bringing of the secreted immune effector molecule into contact with said at least one binding partner is carried out in a container other than the container R, for example in a container T, according to one embodiment, it is the content of the container R that will be suctioned then discharged into the container T using the suction/discharge device. Here again, the binding partner can be contained beforehand in the container T, or else it will be subsequently introduced therein by the suction/discharge device. Said at least one binding partner can be either immobilized at the surface of the containers (R or T), or else it can be present therein in freeze-dried form. According to another embodiment, the binding partner is immobilized at the surface of an endpiece used with the suction/discharge device as, for example, in the context of the kits used with the VIDAS® instrument (SPR® tip). The application of such a partner at the surface of a container or endpiece is widely known to those skilled in the art.

The immunoassay methods are widely known to those skilled in the art and comprise, for example, immunoenzymatic assays or EIA for "Enzyme Linked Immunoassay". Said methods are coupled to a reaction catalyzed by an enzyme using an enzymatic substrate. Depending on the enzymatic substrate chosen, it is possible to have a colorimetric signal (ELISA for Enzyme-Linked Immunosorbent Assay) (Rassasie, M. J. et al., 1992), a fluorescence signal (ELFA technology for Enzyme Linked Fluorescent Assay)

or a chemiluminescent signal (CLIA for Chemiluminescence Immuno Assays) (Stabler T. V., et al., 1991).

The detection of the immune cellular response may be qualitative, semi-quantitative or quantitative. In the context of immunoassays, it is based on measurements which make it possible to quantify the signals emitted during the analysis of the biological sample containing the molecule of interest. The amount of signals that is detected is generally proportional to the amount of molecule of interest to be measured (for example during a sandwich assay, using two binding partners) or inversely proportional to the amount of analyte to be measured (for example during a competition assay, using a single binding partner and a compound which competes with the molecule of interest).

Conventional steps for a sandwich immunoassay in a biological sample, also called test sample, that may contain said analyte or molecule of interest, comprise or consist in:
 bringing together said at least one binding partner and said test sample that may contain the molecule of interest for the binding of the molecule of interest to the binding partner,
 adding a detection partner, which is directly or indirectly coupled to a label, such as an enzyme capable of lyzing an enzymatic substrate, which is for example fluorogenic for an ELFA detection, for binding thereof to the binding partner-molecule of interest complex,
 when the label is an enzyme, bringing together an enzymatic substrate and the complex of binding partner-molecule of interest-detection partner coupled to an enzyme for formation of a reaction medium, and
 detecting, for example by immunofluorescence in the context of an ELFA detection, the presence and/or the amount of molecule of interest by measuring the signal (for example fluorescence) emitted in the reaction medium.

The term "detection partner" is intended to mean any partner capable of binding to the molecule of interest to be detected or quantified, which will be directly or indirectly coupled to a label, for example an enzyme. It may be of the same nature as the binding partner or of a different nature. Examples are given above with the binding partner.

The expression "direct or indirect coupling of the label to the binding partner" is intended to mean that the label is directly bound to the detection partner recognizing the analyte (direct coupling) or else the enzyme is coupled to a binding partner which recognizes the detection partner which itself recognizes the analyte (indirect coupling).

Thus, in the context of direct coupling, the complex formed at the end of the assay, called conjugate, will consist of: "binding partner/molecule of interest/label-coupled detection partner".

In the context of indirect coupling, the complex formed at the end of the assay will consist of: "binding partner/molecule of interest/detection partner/label-coupled binding partner".

The term "label" is intended to mean, in particular, any molecule containing a group which reacts with a group of the detection partner, directly without chemical modification, or after chemical modification so as to include such a group, which molecule is capable of directly or indirectly generating a detectable signal. A nonlimiting list of these direct detection labels consists of:
 enzymes which produce a signal that can be detected, for example by colorimetry, fluorescence, luminescence, such as horseradish peroxidase, alkaline phosphatase, β-galactosidase, glucose-6-phosphate dehydrogenase,
 chromophores such as fluorescent, luminescent, dye compounds,
 radioactive molecules such as $^{32}P$, $^{35}S$ or $^{125}I$,
 fluorescent molecules such as Alexas or phycocyanins, and
 electrochemiluminescent salts such as organometallic derivatives based on acridinium or on ruthenium.

Of course, the binding partner may itself be labeled as indicated above. In the context of a sandwich assay, the second partner used will not then be labeled.

Thus, according to one embodiment, the detection method of the invention is characterized in that step (e) uses a partner for binding to the immune effector molecule which is an immunoassay partner and in that the revealing of the binding or nonbinding of said molecule is carried out by means of a sandwich assay using another partner for binding to the molecule, which may or may not be different in nature, one of the two partners being labeled.

Conventional steps for a competition immunoassay, in a test sample that may contain said molecule of interest, comprise:
 bringing together said at least one binding partner, an analog of the molecule of interest coupled to a label, for example an enzyme capable of lyzing an enzymatic, for example fluorogenic, substrate, and said sample, which compete for the binding to the binding partner,
 when the label is an enzyme, bringing together an enzymatic substrate, binding partner-molecule of interest complexes and binding partner-analog of the molecule of interest complexes, for the formation of a reaction medium, and
 detecting, for example by immunofluorescence, the presence and/or amount of analyte by measuring the signal, for example the fluorescence, emitted in the reaction medium.

The term "analog of the analyte" is intended to mean any molecule which has the same capacities of binding to the binding partner as the molecule of interest.

The label coupled to the analog of the molecule of interest is equivalent to the label that is of use in the context of a sandwich assay.

According to another particular embodiment of the invention, the detection method of the invention is characterized in that step (e) uses a partner for binding to the immune effector molecule which is an immunoassay partner and in that the revealing of the binding or nonbinding of said molecule is carried out by means of a competition assay using a labeled compound which competes with the molecule of interest.

Regardless of the type of method used, of sandwich or competition type, the enzyme is a widely suitable label and mention may in particular be made, as an example, of sulfatase, peroxidase, alkaline phosphatase (ALP), acid phosphatase, glucose oxidase (GOx), glucose-6-phosphate dehydrogenase (G6PD) and β-galactosidase (β-gal). The corresponding enzymatic substrates are widely known to those skilled in the art and comprise, for example, 4-methylumbelliferyl phosphate or 5-bromo-4-chloro-3-indolyl-beta-D-galactopyranoside.

In one particular embodiment, in the detection method according to the invention, the revealing of the analyte is carried out using an enzyme and an enzymatic substrate catalyzed by said enzyme, preferably alkaline phosphatase and 4-methylumbelliferyl phosphate.

When the immune cellular response is obtained by detection of the RNA transcript of the gene of the immune effector molecule, also called target gene, the measurement of its expression level uses RNA detection methods well known to those skilled in the art, by means of conventional instruments such as Filmarray® (bioMérieux), LightCycler1.0, 2.0 and 480 (System II), Applied Biosystems 7500, 7500 Fast, Fast Dx, 7300, ViiA™ 7 Real-Time PCR System, StepOne, Rotor-Gene, Dx Real-Time System and CFX 96 Real-Time System.

Thus, these methods can first of all comprise a preliminary step of extracting the total RNAs from the biological sample (ribosomal RNAs, transfer RNA and messenger RNAs). This step is followed by a step of reverse transcription of these various RNAs in order to obtain their complementary DNA (cDNA). The cDNAs specific for the target gene are then amplified, detected, then quantified.

The extraction is carried out by means of any of the nucleic acid extraction and purification protocols well known to those skilled in the art. By way of indication, nucleic acid extraction can be carried out by lysis of the cells present in the biological sample, followed by a purification, for example on magnetic beads, or else by extraction with phenol, chloroform and alcohol. These steps are well known to those skilled in the art and are described for example in U.S. Pat. No. 5,234,809, EP 0 245 945, WO 93/01312, WO 00/21973, WO 02/16383 or in the technical sheets of the sample preparation (sample prep) kits and platforms MagNa Pure, QiaCube, EasyMAG®, QiaAmp DNA mini Kit.

A reverse transcription reaction is then carried out using a reverse transcriptase enzyme which makes it possible to obtain, from an RNA fragment, a complementary DNA (cDNA) fragment. The implementation of such a step is well known to those skilled in the art (general review, 2003). When it is desired more particularly to obtain only the complementary DNAs of the messenger RNAs, this enzymatic step is carried out in the presence of nucleotide fragments comprising only thymine bases (polyT), which hybridize by complementarity to the polyA sequence of the various mRNAs in order to form a polyT-polyA complex which then serves as a starting point for the reverse transcription reaction carried out by the reverse transcriptase enzyme. Various complementary DNAs of the various messenger RNAs initially present in the biological sample are then obtained.

Next, with the aim of specifically amplifying the cDNAs specific for the target gene, an enzymatic amplification reaction is carried out. An enzymatic amplification reaction is a process that generates multiple copies of a nucleotide fragment through the action of at least one enzyme. Such amplification reactions are well known to those skilled in the art and mention may in particular be made of the following techniques:

PCR (Polymerase Chain Reaction), as described in U.S. Pat. Nos. 4,683,195, 4,683,202 and 4,800,159, and all the variants thereof;

LCR (Ligase Chain Reaction), set out for example in patent application EP 0 201 184;

RCR (Repair Chain Reaction), described in patent application WO 90/01069;

3SR (Self Sustained Sequence Replication) with patent application WO 90/06995;

NASBA (Nucleic Acid Sequence-Based Amplification) with patent application WO 91/02818;

TMA (Transcription Mediated Amplification) with U.S. Pat. No. 5,399,491;

LAMP (Loop mediated isothermal amplification) with U.S. Pat. No. 6,410,278;

SDA (Strand Displacement Amplification) described in Y. Masamute and C. C. Richardson, 1971, J. Biol. Chem. 246, 2692-2701; R. L. Lechner et al., 1983, J. Biol. Chem. 258, 11174-11184; or R. C. Lundquist and B. M. Olivera, 1982, Cell 31, 53-60;

CRCA (cascade rolling circle amplification);

ICAN (isothermal and chimeric primer-initiated amplification of nucleic acids) described in T Uemori, 2007, J Biochem. 2007 August; 142(2):283-92;

HDA (target based-helicase dependent amplification) described in Vincent et al., 2004, Embo reports, 5(8): 795-800.

The term "amplicons" is then used to denote the polynucleotides generated by an enzymatic amplification technique. Preferentially, when the enzymatic amplification is a PCR, the specific reagent comprises at least two specific amplification primers in order to amplify a particular region of the complementary DNA of the mRNA from the target gene. When the enzymatic amplification is a PCR carried out after a reverse transcription reaction, the term used is "RT-PCR". Among the PCR variants, mention may in particular be made of the nested polymerase chain reaction (or Nested-PCR) which involves two PCR amplifications through the presence of two successive PCRs and two different pairs of primers: the first pair of primers is used for the first PCR (conventional PCR), the second pair of primers being used during the second PCR and being defined such that it hybridizes to a sequence present in the amplification product (amplicon) of the first PCR.

Following this amplification step, regardless of the technique used, the expression level of the target gene is determined for example by hybridization using at least one hybridization probe specific for the expression product of this target gene, which corresponds to the partner for binding to the RNA transcript of interest, or using a double-stranded DNA-intercalating agent such as SybrGreen®.

The term "hybridization probe" is intended to mean a nucleotide fragment comprising from 5 to 100 nucleotide units, in particular from 6 to 35 nucleotide units, having a hybridization specificity under determined conditions so as to form a hybridization complex with a target nucleotide fragment. In the present invention, the target nucleotide fragment may be a nucleotide sequence included in a messenger RNA or a nucleotide sequence included in a complementary DNA obtained by reverse transcription of said messenger RNA.

The hybridization techniques are well known to those skilled in the art, and mention may in particular be made of the Northern blot technique.

The quantification of the mRNAs, expression products of the target gene, involves a step of detecting the hybridization reaction, between the hybridization probe or the DNA-intercalating agent and the target nucleotide fragment.

The term "detection" is intended to mean either a direct detection by a physical method, or a detection method using a label. Numerous detection methods exist for the detection of nucleic acids (Keller G. H., 1993; Kricka, 1999).

Those skilled in the art will be able to refer in particular to the publications by Bustin S A and Giulietti A et al. (Bustin S A, 2002; Giulietti A, 2001).

Everything that has been described above relating to the immunoassays, as regards the various steps of the method and the use of a binding partner, can be applied to the detection by molecular biology.

The detection method of the invention may also comprise one or more additional steps of rinsing after each step, such as for example:

before the addition of the detection partner, a rinsing step so as to remove the molecule not bound to the binding partner-molecule of interest complex; and after the addition of the detection partner, a rinsing step so as to remove the unbound detection partner.

The rinsing steps are steps known to those skilled in the art. They are carried out with buffers that are compatible with the reaction medium and the reading of the signal.

Steps (a) to (d) are of course carried out before step (e), but several embodiments are possible. Thus, the detection method of the invention comprises one or more of the following features:

steps (a) to (e) are carried out with the same instrument;

steps (a) to (e) are carried out successively on the same day;

steps (a) to (d) are carried out on a first day or over the course of several days, for example up to 3 days, as defined above, and step (e) is then carried out on another day, for example 1, 2 or 3 days later.

The term "same instrument" is intended to mean the same instrument for carrying out all the steps successively, or else two instruments from the same range, one for bringing together said at least one stimulant and the biological sample as taken, and the other for detecting the immune cellular response. Thus, by virtue of the use of the same instrument, the method is completely automated using a simplified piece of equipment which requires neither the presence of highly qualified personnel, nor the implementation of very specific conditions when the incubation step is carried out under nonsterile conditions. In this particular embodiment, the suction/discharge device may be used to transfer the biological sample containing the secreted molecule of interest to the container(s) used for step (e), as indicated above. The various container(s) required for carrying out all the steps of the method of the invention may be inserted in the instrument before step (a) or else they may be inserted in two steps, as a function of the phase (stimulation/detection).

The examples of instruments that can be used comprise all the diagnostic instruments that are already commercially available, for example the immunoassay or molecular biology instruments, which comprise:

A suction/discharge device for taking the biological sample from a patient and placing it in a container for the stimulation, then subsequently for detecting the immune cellular response, A set of containers for being able to carry out the stimulation and the detection, Optionally a system for maintaining the temperature of the container being used for the incubation at the selected temperature, and A system for detecting the immune cellular response.

Nonlimiting examples of suitable immunoassay instruments comprise the instruments of the VIDAS® range, such as VIDAS®, miniVIDAS®, VIDAS® 3 (bioMérieux), Simoa® HD-1 (Quanterix), Cobas® or Elecsys® (Roche Diagnostic Gmbh), LIAISON® (Diasorin), Architect® (Abbott), Access 2 (Beckham Coulter), Clarity™ (Singulex®) and Vitros® (Johnson & Johnson).

For example, the instrument of the VIDAS® range (bioMérieux) uses a suction/discharge device consisting of a tip (SPR®) on a support, which tip is coated with a binding partner, a strip comprising 10 wells (thus 10 containers), including one sample well, a well for the stimulation, a well for reading the signal representative of the detection of the immune effector molecule and wells that contain the various constituents, for example those required for the stimulation and for the immunoassay carried out for detecting the immune cell culture. This instrument also has a system for regulating the temperature of the wells of the strip. The VIDAS® 3 instrument also has an arm fitted with an endpiece.

As indicated above, the method for detecting the immune cellular response of the invention can be divided into two phases, the first phase of which constitutes another subject of the invention, which is an automated method for stimulating at least one cell capable of secreting an immune effector molecule for the secretion of said molecule, said at least one cell being from a biological sample of animal origin, characterized in that it comprises or consists of the steps consisting in:

(a) suctioning a defined amount of the biological sample as taken by means of an automated suction/discharge device, (b) discharging this defined amount, using said automated suction/discharge device, into a container R, said container R containing, beforehand, at least one stimulant for secretion of said molecule by said at least one cell, or else said container R not containing such an at least one stimulant, (c) when the container does not contain, beforehand, at least one secretion stimulant, introducing into said container R using said automated suction/discharge device said at least one secretion stimulant contained in a container E, and (d) allowing the defined amount of sample and said at least one stimulant to incubate, forming a mixture, for the secretion of said molecule by said at least one cell (i) in said container R or (ii) in another container S after suctioning and discharge of said mixture using said automated suction/discharge device.

The features linked to the biological sample, to the cells to be cultured, to the immune effector molecule, also called molecule of interest or else analyte, to the diseases of interest, to the stimulation/incubation conditions, with or without pathogen-specific stimulant(s), to the automation devices used, to the methods for detecting the immune response, etc., as described above in the context of the detection method of the invention, also apply for the stimulation method.

The molecule thus obtained by automated stimulation and detection thereof are particularly of use in the medical field. Thus, the invention also relates to the use of the method for detecting an immune cellular response or of the automatic stimulation method, as described above, for the diagnosis and monitoring of pathological conditions, for medicament and vaccine toxicity studies and for determining the immune status of a patient.

The pathological conditions in question have been described above. In parallel, it is important for the medicaments and vaccines, which may be future ones, not to be toxic and for the methods of the invention to be able to be used in this sense. Finally, since the immune status of a patient is evaluated by the capacity of the cells involved in the immune response to secrete immune effector molecules, the method of the invention is particularly suitable for this purpose.

The invention will be understood more clearly by means of the following examples which are given by way of nonlimiting illustration, and also by means of FIG. 1 which is a schematic representation of the tip and of the strip that are used with the VIDAS® instrument, the tip belonging to the suction/discharge device for suctioning and discharging the defined amount of biological sample in a stimulation well.

EXAMPLES

Example 1: Automation of the Stimulation Step, Taking of Total Blood Sample, Stimulation with a Nonspecific Stimulant, Assaying of Interferon Gamma 1.1. Carrying Out the Secretion Step The blood samples used in this example were obtained from the Etablissements Français du Sang (EFS) [French National Blood Bank] and collected from healthy donors. Five blood samples were taken sterily in Vacutainer® tubes (Becton-Dickinson) containing lithium heparinate or equivalent reference from another supplier.

These samples were stimulated according to two conditions (1 and 2)

Condition 1: Stimulation in a Tube, According to the Prior Art—Sterile Stimulation Conditions.

For this condition, sterile dry tubes (Cat. No. 367614, Becton-Dickinson) are used. Under sterile conditions, under a laminar flow hood, each blood sample is stimulated in three different ways:

Assay 1: PBS tube (negative control): 400 µl of PBS buffer are mixed with 400 µl of total blood.

Assay 2: Phorbol 12-myristate 13-acetate (PMA)-phytohemagglutinin (PHA) tube: 400 µl of PMA (2.30 ng/ml) and PHA (0.46 µg/ml) stimulants are mixed with 400 µl of total blood.

Assay 3: Phorbol 12-myristate 13-acetate (PMA)-phytohemagglutinin (PHA) tube: 400 µl of PMA (25 ng/ml) and PHA (5 µg/ml) stimulants are mixed with 400 µl of total blood.

The tubes were re-stoppered under a hood and then incubated vertically at 37° C. for 17 hours 30 minutes.

Condition 2: Automated Stimulation in a VIDAS® Cartridge—Nonsterile Stimulation Conditions.

The strip of the VIDAS® immunoanalysis automated device is described in FIG. 1. Said strip (11) is composed of 10 wells (1 to 10) partially covered with a labeled sealed aluminum foil (not shown). The last well (10) is an optical cuvette in which the fluorescence is measured, and contains the enzymatic substrate. The various reagents required for the stimulation and/or the analysis, such as the stimulant (in this case PBS wells or PMA-PHA wells), the washing solutions or the revealing antibodies, are contained in the various other wells (1 to 9).

The strips thus prepared were inserted into the VIDAS® 3 automated device along with the tubes of total blood taken from the donors. Before loading the tubes in the automated device, their stopper is removed. From this moment, the total blood samples are no longer processed under sterile conditions. The VIDAS® 3 instrument was programmed in order to automatically carry out the following steps:

1) Suctioning, by means of the suction/discharge device, a precise volume of total blood (400 µl) from the primary sample tube,
2) Piercing the aluminum foil which covers the stimulation well using the suction/discharge device,
3) Discharging the total blood into the stimulation well,
4) Incubating the cartridge at 37° C. for 17 h 30 min.

Following this stimulation step, the VIDAS® 3 can automatically link said step to the step of detecting the secreted IFNγ according to the procedure described hereinbelow in section 1.2.

The conditions for stimulation in a sterile tube (tube) or in the VIDAS® strip (well) are summarized in Table 1 hereinafter.

TABLE 1 conditions for sterile-tube stimulation or automated-device-well stimulation

| Conditions | Stimulation container | Secretion stimulant |
|---|---|---|
| PBS | Tube | PBS (negative control) |
| PMA-PHA low concentration | Tube | PMA 2.30 ng/ml + PHA 0.46 µg/ml in PBS |
| PMA-PHA high concentration | Tube | PMA 25 ng/ml + PHA 5 µg/ml in PBS |
| PBS | Well | PBS (negative control) |
| PMA-PHA low concentration | Well | PMA 2.30 ng/ml + PHA 0.46 µg/ml in PBS |
| PMA-PHA high concentration | Well | PMA 25 ng/ml + PHA 5 µg/ml in PBS |

PMA: phorbol 12-myristate 13-acetate
PHA: phytohemagglutinin 1.2. IFNγ Detection Step: Automated Immunoassay Procedure Detection Principle The detection of the IFNγ in the biological samples is carried out by one-step sandwich immunoassay using the VIDAS® immunoanalysis automated device (bioMérieux). The single-use tip (represented as 12 in FIG. 1) serves both as solid phase for the reaction and as pipetting system. It is used in combination with the strip (11), as described in point 1.1 above. All the steps of the test are thus carried out automatically by the instrument. They consist of a succession of cycles of suction/discharge of the reaction medium.

Sensitization and Passivation of the Tips.

The tips were sensitized with 270 µl of a solution of first anti-IFNγ monoclonal antibody (4G1E12, bioMérieux, France) at 5 µg/ml in a carbonate buffer. After approximately 6-8 h of incubation at +18/25° C. with the sensitizing solution, the tips were emptied. Next, 300 µl of phosphate buffer containing 10 g/l of bovine albumin are added for the passivation of the tips at +18/25° C. for approximately 18-24 h. The tips are then emptied, dried, then stored at +4° C. until use, in the dry.

Preparation of the Conjugated Antibody Solutions.

The solution of conjugate (detection partner) contains a second anti-IFNγ monoclonal antibody coupled to alkaline phosphatase (2A4B11, bioMérieux). The conjugated antibodies were diluted to approximately 500 ng/ml in a phosphate/BSA buffer.

Immunoassay.

As soon as the VIDAS® tip is in contact with the sample, the immunological reaction begins since the capture antibodies are immobilized on this tip. The automated device mixes the sample to be tested (100 µl—in the present case the blood after stimulation) with 250 µl of the solution of conjugate. The incubation lasts approximately 10 minutes at 37° C. and allows the specific binding of the IFNγ to, on the one hand, the antibody adsorbed onto the tip (capture antibody) and to, on the other hand, the conjugated antibody (detection antibody). The nonbound components are then removed by means of three washes with a Tris NaCl buffer. During the final revealing step, the 4-methylumbelliferyl phosphate substrate is suctioned then discharged in the tip; the enzyme of the conjugated antibody catalyzes the reaction for hydrolysis of this substrate to 4-methylumbelliferone, the emitted fluorescence of which is measured at 450 nm. The fluorescence signal value (RFV: relative fluorescence value) is proportional to the concentration of the antigen present in the sample.

The results of the assays are presented in Table 2:

TABLE 2 measurement of IFNγ by VIDAS

| Sample code | Stimulation container | IFNγ measurement by VIDAS Signal in RFV | | | PMA-PHA high concentration/ PBS ratio | PMA-PHA low concentration/ PBS ratio |
| --- | --- | --- | --- | --- | --- | --- |
| | | PBS | PMA/PHA high concentration | PMA/PHA low concentration | | |
| 0312274 | Tube | 23 | 11447 | 229 | 498 | 10 |
| | Well | 11 | 11516 | 72 | 1047 | 7 |
| 0312370 | Tube | 15 | 11319 | 111 | 755 | 7 |
| | Well | 8 | 10928 | 48 | 1366 | 6 |
| 0312397 | Tube | 26 | 11216 | 767 | 431 | 30 |
| | Well | 16 | 13588 | 543 | 43.6 | 34 |
| 0312303 | Tube | 16 | 11306 | 610 | 707 | 38 |
| | Well | 7 | 8905 | 172 | 1272 | 25 |

A very strong secretion of IFNγ (signals >8000 RFV) is observed when the cells are stimulated using a high concentration of PHA in the PMA/PHA mixture, whereas the secretion is moderate (signals <800 RFV) if the PHA concentration is low in the PMA/PHA mixture. This phenomenon is observed both for the stimulation carried out in the tube and for that carried out in the well.

The nonspecific secretion in the absence of stimulant (PBS assay) is very low in the tube (signals <30 RFV) and virtually nonexistent in the well (signals <20 RFV).

The IFNγ secretion level obtained after stimulation is compared to that measured in the absence of stimulant by calculating a ratio between the two measurements. If the ratio is at least 3, a positive conclusion is drawn.

When the stimulation is carried out in the well, the ratios range from 6 to 1366, whereas, when the stimulation is carried out in the tube, the ratios range from 7 to 755. It can thus be concluded that the stimulation causing the IFNγ secretion is equivalent in the well and the tube or is better in the well than in the tube.

Example 2: Automation of the Stimulation Step, Taking of Total Blood Sample, Stimulation with a Specific Stimulant (*Mycobacterium tuberculosis* Antigens), Assaying of Interferon Gamma The blood samples used in this example were obtained from Biotech Bank (Angers, France) and collected either from individuals having had tuberculosis or from their close entourage. Four blood samples were taken sterily in Vacutainer® tubes (Becton-Dickinson) containing lithium heparinate or an equivalent reference from another supplier.

Each blood sample was stimulated according to three different protocols detailed in Table 3 hereinafter, using as stimulation agent the content of the Quantiferon® TB tubes (Cat. No. T0590-0301, Qiagen). The Quantiferon® TB tubes are particular vacuum blood sampling tubes which make it possible to collect the total blood under perfectly sterile conditions. There are three of them:

The AG tube, for antigen, contains peptides derived from the ESAT-6, CFP-10 and TB7.7 proteins of *Mycobacterium tuberculosis*; it is the tube for the specific stimulation. If there is IFNγ secretion in this tube, it is because the sample contains T cells which are capable of specifically reacting against the *M. tuberculosis* peptides.

The NIL tube corresponds to the negative control and the MIT tube, which contains a mitogen, corresponds to the positive control.

Each sample was stimulated by the content of the two Quantiferon AG and NIL tubes and according to two protocols, which corresponds to a total of four conditions per sample.

In routine use, according to the manufacturer's instructions, 0.8 to 1.2 ml of total blood are directly taken sterily on Quantiferon® TB tubes and the stimulation phase is carried out sterily in the tubes containing beforehand the secretion stimulants. The samples thus stimulated are then centrifuged and the interferon gamma detection is carried out, in a microplate, in the plasma thus obtained. However, in order to be able to perform the comparison with the automated stimulation, this procedure was slightly modified, as indicated in Table 3:

TABLE 3 interferon gamma stimulation and detection conditions

| | |
| --- | --- |
| Reference condition CENTRIFUGATION | 1. Under a laminar flow hood, under sterile conditions: add 400 μl of PBS to each Quantiferon tube, then add 400 μl of blood<br>2. Invert the tubes 10 times in order to mix<br>3. Incubate in the vertical position at 37° C. for 17 h 30<br>4. Centrifugation for 15 min at 1800 g<br>5. IFNγ detection in the plasma by VIDAS |
| Automated condition, according to the invention | 1. Add 400 μl of PBS to each Quantiferon tube<br>2. Invert the tubes 10 times in order to mix<br>3. Recovery of 400 μl of stimulant for transfer into the stimulation well of the VIDAS cartridge<br>4. Launching of the automated stimulation program (nonsterile) + incubation + assay on VIDAS:<br>   Automatic suction of 2 × 200 μl of total blood from the primary tube<br>   Discharge of the 400 μl in the stimulation well<br>   Incubation at 37° C. for 17 h 30<br>   IFNγ detection in the sample thus stimulated by VIDAS |

The detection of IFNγ in the blood samples after the stimulation was carried out according to the procedure detailed in section 1.2 of Example 1.

The results (RFV signal measured using VIDAS® according to the experimental conditions) are given in Table 4 below:

TABLE 4 measurement of IFNγ by VIDAS

| Patient code | Stimulation protocol | IFNγ measurement by VIDAS Signal in RFV | | AG/NIL Ratio | Interpretation |
|---|---|---|---|---|---|
| | | NIL | ANTIGEN (AG) | | |
| BK-37 | Reference | 104 | 118 | 1.1 | Neg |
| | Automated | 121 | 204 | 1.7 | Neg |
| BK-38 | Reference | 14 | 15 | 1.1 | Neg |
| | Automated | 11 | 14 | 1.3 | Neg |
| BK-39 | Reference | 53 | 482 | 9.1 | Pos |
| | Automated | 31 | 1351 | 43.6 | Pos |
| BK-40 | Reference | 67 | 354 | 5.3 | Pos |
| | Automated | 64 | 268 | 4.2 | Pos |
| BK-33 | Reference | 42 | 118 | 2.8 | Neg |
| | Automated | 45 | 48 | 1.1 | Neg |
| BK-34 | Reference | 98 | 98 | 1.0 | Neg |
| | Automated | 113 | 142 | 1.3 | Neg |
| BK-20 | Reference | 179 | 1083 | 6.1 | Pos |
| | Automated | 114 | 1954 | 17.1 | Pos |

Results:

The automated protocol for stimulation and detection of the immune cellular response, without centrifugation and under nonsterile conditions, makes it possible to obtain signals (11-1954 RFV) equivalent to or greater than those obtained with the sterile-tube reference protocol (14-1083 RFV). The AG/NIL ratio ranges from 1.1 to 43.6 for the automated condition and from 1.1 to 17.1 for the reference condition, which reflects an equivalent or greater specific stimulation under the automated condition.

The samples BK-37, BK-38, BK-33 and BK-34 have AG/NIL ratios which range between 1.0 and 2.8 under the two conditions tested. The detected IFNγ secretion level is basal (ratio <3) and is not specific for the *M. tuberculosis* antigens. Consequently, the automated condition and the reference condition make it possible to conclude that these patients were not infected with *M. tuberculosis*: negative interpretation (Neg).

The sample BK-40 exhibits highly corresponding AG/NIL ratios between 4.2 and 5.3 depending on the stimulation protocol. In this sample, IFNγ secretion (ratio >3) specifically triggered by the *M. tuberculosis* antigens is observed. It can be concluded that the BK-40 patient has already been infected with *M. tuberculosis*: positive interpretation (Pos). The same interpretation is obtained for the samples BK-39 and BK-20 for which the highest specific IFNγ secretion levels are demonstrated. For these patients, the AG/NIL ratios are not equivalent between the two conditions: ratios of 43.6 and 17.1 are respectively observed for the automated condition compared with 9.1 and 6.1 for the reference condition, which shows an improved analytical sensitivity for the automated condition, without a centrifugation step and under nonsterile conditions with a calibrated amount of blood, compared with the reference condition (sterile conditions with amount of blood which varies).

Example 3: Automation of the Stimulation Step, Taking of Total Blood Sample, Nonspecific PMA+PHA Stimulation, TNF Alpha Assay 3.1. Implementation of the Secretion Step The blood samples used in this example were obtained from the Etablissements Français du Sang (EFS) [French National Blood Bank] and collected from healthy donors. Two blood samples were taken sterily into Vacutainer® tubes (Becton-Dickinson) containing lithium heparinate or equivalent reference from another supplier, and stimulated either in a tube (reference sterile condition), or in a VIDAS® well (according to the invention) according to the procedure described in section 1.1.

The conditions for sterile-tube stimulation (tube) or stimulation in the VIDAS® strip (well) are summarized in Table 5 below:

TABLE 5 conditions for sterile-tube stimulation or automated-device-well stimulation

| Conditions | Stimulation container | Secretion stimulant |
|---|---|---|
| PBS | Tube | PBS (negative control) |
| PMA-PHA high concentration | Tube | PMA 25 ng/ml + PHA 5 µg/ml in PBS |
| PBS | Well | PBS (negative control) |
| PMA-PHA high concentration | Well | PMA 25 ng/ml + PHA 5 µg/ml in PBS |

At the end of the stimulation step, the sample is taken in order to measure the TNFα concentration with the Quantikine® HS ELISA human TNFα immunoassay kit from R&D Systems (Cat No. HSTA00D) by applying the procedure recommended by the producer (instruction sheet version 12/13).

3.2. Results of the TNF Alpha Assay

The experimental results obtained are presented in Table 6 below:

TABLE 6

TNFα measurement by ELISA

| Sample code | Stimulation container | TNFα measurement by ELISA in pg/ml | | PMA-PHA high concentration/ PBS ratio |
|---|---|---|---|---|
| | | PBS | PMA/PHA high concentration | |
| 59171003916 | Tube | 2.15 | >32 | >14.9 |
| | Well | 2.95 | >32 | >10.8 |
| 5917100373- | Tube | 1.33 | >32 | >24.1 |
| | Well | 0.97 | >32 | >33.0 |

As shown in Table 6, a very strong TNFα secretion (concentration greater than 32 pg/ml) is observed when the cells are stimulated using a high concentration of PHA in the PMA/PHA mixture. This phenomenon is observed both for the stimulation carried out in the tube and for that carried out in the well.

The nonspecific secretion in the absence of stimulant (PBS assay) is very weak both in the tube and in the well (concentration <3 pg/ml).

When the stimulation is carried out in the well, the ratios are 10.8 and 33, comparable to those calculated when the stimulation is carried out in the tube, respectively 14.9 and 24.1. It can thus be concluded that the TNFα secretion was stimulated by the PMA-PHA mixture in an equivalent manner in the tube and in the well.

Example 4: Automation of the Stimulation Step, Taking of Total Blood Sample, Nonspecific LPS Stimulation, TNF Alpha Assay 4.1. Implementation of the Secretion Step The blood samples used in this example were obtained from the Etablissements Français du Sang (EFS) [French National Blood Bank] and collected from healthy donors. Two blood samples were taken sterily into Vacutainer® tubes (Becton-Dickinson) containing lithium heparinate or equivalent reference from another supplier.

The samples were stimulated either in a tube (REF sterile condition), or in a VIDAS® well (according to the invention) according to the procedure described in section 1.1 of example 1, with the only difference being that the PMA+PHA mixture was replaced with a mixture in equal parts of *E. coli* lipopolysaccharides (LPS, Sigma, Cat. No. L3012, L2637 and L3137). The stimulation conditions are reproduced in Table 7:

TABLE 7

| conditions for sterile-tube stimulation or automated-device-well stimulation | | |
|---|---|---|
| Conditions | Stimulation container | Secretion stimulant |
| PBS | Tube | PBS (negative control) |
| LPS | Tube | LPS 50 ng/ml |
| PBS | Well | PBS (negative control) |
| LPS | Well | LPS 50 ng/ml |

At the end of the stimulation step, the sample is taken in order to measure the TNF alpha concentration with the Quantikine® HS ELISA human TNF alpha immunoassay kit from R&D systems (Cat. No. HSTA00D) by applying the procedure recommended by the producer (instruction sheet version 12/13).

4.2. Results of the TNF Alpha Assay

The experimental results obtained are presented in Table 8:

TABLE 8

| | | TNFα measurement by ELISA | | |
|---|---|---|---|---|
| | | TNFα measurement by ELISA in pg/ml | | PMA-PHA high |
| Sample code | Stimulation container | PBS | PMA/PHA high concentration | concentration/ PBS ratio |
| 59171003916 | Tube | 2.15 | >32 | >14.9 |
| | Well | 2.95 | >32 | >10.8 |
| 5917100373- | Tube | 1.33 | >32 | >24.1 |
| | Well | 0.97 | >32 | >33.0 |

As shown in Table 8, a very strong TNFα secretion (concentration >32 pg/ml) is observed when the cells are stimulated using LPS. This phenomenon is observed both for the stimulation carried out in the tube and for that carried out in the well.

The nonspecific secretion in the absence of stimulant (PBS assay) is very weak both in the tube and in the well (concentration <3 pg/ml).

When the stimulation is carried out in the well, the ratios are 10.8 and 33, comparable with those calculated when the stimulation is carried out in the tube, respectively 14.9 and 24.1. It can thus be concluded that the TNFα secretion was stimulated by LPS in an equivalent manner in the tube and in the well.

Example 5: Automation of the Stimulation Step, Taking of Total Blood Sample, Stimulation with a Specific Stimulant (Cytomegalovirus Antigens), Interferon Gamma Assay The blood samples used in this example were obtained from the Etablissements Français du Sang (EFS [French National Blood Bank] Rhône-Alpes, France). Thirteen blood samples were taken sterily into Vacutainer® tubes (Becton-Dickinson) containing lithium heparinate or equivalent reference from another supplier.

Each blood sample was stimulated according to the "Automated condition, according to the invention" protocol described in Table 3 of example 2 using, as stimulating agent, the content of the Quantiferon® CMV tubes (Cat. No. 0192-0301, Qiagen). The Quantiferon® CMV tubes are particular vacuum blood sampling tubes, which make it possible to collect total blood under perfectly sterile conditions. There are three of them:

The AG, for antigen, tube contains Cytomegalovirus peptides; it is the tube for the specific stimulation. If there is INFγ secretion during this stimulation, this means that the blood sample contains T cells which are capable of reacting specifically against the Cytomegalovirus peptides.

The NIL tube corresponds to the negative control and the MIT tube, which contains a mitogen, corresponds to the positive control.

Each sample was stimulated by the content of the Quantiferon AG and NIL tubes.

The detection of IFNγ in the blood samples after stimulation was carried out according to the procedure detailed in section 1.2 of example 1.

The results (RFV signal measured by VIDAS® according to the experimental conditions) are given in Table 9 below.

TABLE 9

| IFNγ measurement by VIDAS ® | | | | |
|---|---|---|---|---|
| | IFNγ measurement by VIDAS ® RFV signal | | | |
| Sample code | NIL | ANTIGEN (AG) | AG/NIL ratio | Interpretation |
| 59180446129 | 87 | 90 | 1.0 | Neg |
| 59180447383 | 24 | 26 | 1.1 | Neg |
| 59180447498 | 11 | 15 | 1.4 | Neg |
| 59180447500 | 47 | 41 | 0.9 | Neg |
| 59180404025 | 12 | 2505 | 209 | Pos |
| 59180404005 | 25 | 26 | 1.0 | Neg |
| 59180404324 | 3 | 2325 | 775 | Pos |
| 59180808113 | 20 | 27 | 1.4 | Neg |
| 59180404076 | 23 | 7463 | 324 | Pos |
| 59174894224 | 9 | 12053 | 1339 | Pos |
| 59174894208 | 14 | 54 | 3.9 | Neg |
| 59174890039 | 98 | 1686 | 17.2 | Pos |
| 59174890020 | 26 | 29 | 1.1 | Neg |

Results:

The automated protocol for stimulation and detection of the immune cellular response, without centrifugation and under nonsterile conditions, makes it possible to obtain signals from 3 to 12 053 RFV and AG/NIL ratios ranging from 0.9 to 1339.

Samples 59180446129, 59180447383, 59180447498, 59180447500, 5918040405-, 59180404113, 59174894208 and 59174890020 have AG/NIL ratios which range between 0.9 and 3.9. The IFNγ secretion level detected is basal (ratio <5) and is not induced by the Cytomegalovirus peptides. Consequently, the stimulation under automated conditions makes it possible to conclude that these patients have not been infected by the Cytomegalovirus: negative interpretation (Neg).

Samples 59180404025, 59180404324, 59180404076, 59174894224 and 59174890039 have AG/NIL ratios between 17.2 and 1339. In these samples, IFNγ secretion (ratio >5) specifically triggered by the Cytomegalovirus peptides is observed. Consequently, the stimulation under automated conditions makes it possible to conclude that these patients have been infected by Cytomegalovirus: positive interpretation (Pos).

Example 6: Automation of the Stimulation Step, Taking of Total Blood Sample, Stimulation with a Specific Stimulant (Epstein-Barr Virus Antigens)

The blood samples used in this example were obtained from the Etablissements Français du Sang (EFS, Rhône-Alpes, France). Ten blood samples were taken sterily in Vacutainer® tubes (Becton-Dickinson) containing lithium heparinate or equivalent reference from another supplier.

Each blood sample was stimulated according to the "Automated condition, according to the invention" protocol described in Table 3 of example 2 using, as stimulating agent, Epstein-Barr virus peptides (Pep Tivator®). For the NIL condition, the sample was brought into contact solely with PBS.

The detection of IFNγ in the blood samples after stimulation was carried out according to the procedure detailed in section 1.2 of example 1.

The results (RFV signal measured by VIDAS® according to the experimental conditions) are given in Table 10 below.

TABLE 10

IFNγ measurement by VIDAS ®

| Sample code | IFN g measurement by VIDAS ® Siganl in RFV | | AG/NIL ratio | Interpretation |
| --- | --- | --- | --- | --- |
| | NIL | ANTIGEN (AG) | | |
| 59174878275 | 19 | 727 | 38.3 | Pos |
| 59174878101 | 49 | 1382 | 28.2 | Pos |
| 59174878136 | 37 | 4838 | 131 | Pos |
| 59174878208 | 47 | 21 | 0.4 | Neg |
| 59174878179 | 7 | 832 | 119 | Pos |
| 59180477726 | 15 | 268 | 17.9 | Pos |
| 59180477734 | 11 | 22 | 2.0 | Neg |
| 59180477718 | 32 | 1263 | 39.5 | Pos |
| 59180477697 | 83 | 79 | 1.0 | Neg |
| 5918047770 | 41 | 1163 | 28.4 | Pos |

Results:

The automated protocol for stimulation and detection of the immune cellular response, without centrifugation and under nonsterile conditions, makes it possible to obtain signals of 7 to 4838 RFV and AG/NIL ratios ranging from 0.4 to 131.

Samples 59174878208, 59180477734 and 59180477697 have AG/NIL ratios which vary between 0.4 and 2.0. These ratios are low (<4), which means that the IFNγ secretion is not linked to the EBV virus peptides. Consequently, the stimulation under the automated conditions makes it possible to conclude that these patients have not been infected with the Epstein-Barr virus: negative interpretation (Neg).

The samples 59174878275, 59174878101, 59714878136, 59174878179, 59180477726, 59180477718 and 5918047770—have AG/NIL ratios between 17.9 and 131. These ratios are high (>4), which means that the IFNγ secretion is specifically linked to the Epstein-Barr virus peptides. Consequently, the stimulation under the automated conditions makes it possible to conclude that these patients have been infected with the Epstein-Barr virus: positive interpretation (Pos).

Example 7: Automation of the Stimulation Step, Taking of Total Blood Sample, Nonspecific LPS Stimulation, Assay by Molecular Biology The blood samples used in this example were obtained from the Etablissements Français du Sang (EFS, Rhône-Alpes, France). Five blood samples were taken sterily into Vacutainer® tubes (Becton-Dickinson) containing lithium heparinate or equivalent reference from another supplier.

Each blood sample was stimulated according to the "Automated condition, according to the invention" protocol described in Table 3 of example 2, using LPS as stimulating agent. For the NIL condition, the sample was brought into contact only with PBS.

Detection of the immune cellular response by quantification of the mRNAs of the following genes: IFNγ gene, IL1β gene and ZAP70 gene (bioMérieux internal kits), in the blood samples after stimulation, was carried out as follows: the mRNAs were extracted after lysis of 100 µl of the reaction mixture using an automated method (BOOM technology). The mRNAs were then amplified by two-step RT-nested PCR (1st PCR of 26 cycles, followed by a 2nd PCR of 35 cycles). The actual detection was carried out using an intercalating agent and the real-time measurements were acquired in order to construct an amplification curve and to obtain a point Cp (crossing point) for each target and for the three reference genes (DECR1, PPIB & FPGS). The signal, corresponding to the mRNA expression level, was standardized by subtracting, from the target Cp, a geometric mean of the three reference genes.

The results (standardized Cp values±standard deviation) are given in table 11 hereinafter. The lower the standardized Cp value, the higher the expression level.

TABLE 11

| | Standardized CP values ± SD | | |
| --- | --- | --- | --- |
| | NIL | LPS | P-value |
| IFN-γ | 5.33 ± 0.88 | 3.12 ± 1.19 | 0.0159 |
| IL1B | −4.37 ± 4.04 | −7.90 ± 0.69 | 0.1508 |
| ZAP70 | −1.75 ± 0.61 | −2.14 ± 0.86 | 0.5476 |

The results in Table 11 below show that it is possible to detect an immune cellular response by means of a molecular biology test after automated stimulation according to the invention.

LITERATURE REFERENCES

Almeida C A. M. et al., 2009, Journal of Immunological Methods, 344: 1-5
Boersma Y L and Plütckthun A, 2011, Curr. Opin. Biotechnol, 22: 849-857
Bustin S A, 2002, Journal of molecular endocrinology, 29: 23-39
Coligan J. E., 1994, Current Protocols in Immunology, Volume I, Supplement 10, Unit 6.19: 1-8
Cox J. H. et al., 2006, Methods, 38: 274-282
Ellingdon A D and Szostak J W., 1990, Nature, 346: 818-822
Gaur R L, et al., 2013, Journal of Clinical Microbiology, 51(11): 3521-3526
Giulietti A et al., 2001, Methods, 25: 386-401
Handbook of Elispot, 2005, Methods and Protocols, Humana Press Totowa, New Jersey, 1-321
Keller G H and Manak M M, 1993, DNA Probes, p. 137-196. Stockton Press, Stockton Press
Kricka L J, 1999, Nucleic acid detection technologies—labels, strategies and formats, Clin. Chem. 45, 453-458
Lalvani, A., 2007, Chest, 131: 1899-1906
Neubauer J. C. et al., 2017, Cytotechnology, 69(1): 57-73
Pal M. et al., 2014, Clin. Microbiol. Rev., 27(1): 3-20
Rassasie M. J. et al., 1992, Steroids, 57: 112
Revue generale, 2003, Ann Biol Clin, 61: 635-44
Stabler T. V., et al., 1991, Clin. Chem. 37(11): 1987
Uemori T, 2007, J Biochem. August, 142(2): 283-92
Vincent et al., 2004, Embo reports, 5(8): 795-800
Wood P. R., 1990, Research in Veterinary Science, 49: 46-49

The invention claimed is:

1. An automated stimulation method for stimulating a cell capable of secreting an immune effector molecule for the secretion of the molecule, the method comprising:
    suctioning a defined amount of total blood, as taken from an animal organism, using an automated suction/discharge device, wherein the defined amount of the total blood contains the cell capable of secreting the immune effector molecule;
    discharging the defined amount of the total blood, using the automated suction/discharge device, into a first container R that optionally already contains a stimulant for secretion of the molecule by the cell;
    when the first container R does not already contain the secretion stimulant, introducing the secretion stimulant into the first container R containing the discharged defined amount of the total blood, using the automated suction/discharge device; and
    allowing the defined amount of the total blood and the secretion stimulant to incubate under nonsterile conditions, forming a mixture, for the secretion of the molecule by the cell either (i) in the first container R or (ii) in a second container S after suctioning and discharge of the mixture using the automated suction/discharge device,
    wherein the automated stimulation method is performed under nonsterile conditions and the mixture is configured for use in detecting an immune cellular response.

2. The automated stimulation method of claim 1, wherein the secretion stimulant is a nonspecific stimulant or a stimulant specific for a pathogenic microorganism.

3. The automated stimulation method of claim 1, wherein the total blood is of human, bovine, canine, feline, or equine origin.

4. An automated stimulation and detection method for detecting an immune cellular response in total blood as taken from an animal organism, the method comprising:
    suctioning a defined amount of the total blood as taken, using an automated suction/discharge device, wherein the defined amount of the total blood may contain a cell capable of secreting an immune effector molecule;
    discharging the defined amount of the total blood, using the automated suction/discharge device, into a first container R that optionally already contains a stimulant for secretion of the molecule by the cell;
    when the first container R does not already contain the secretion stimulant, introducing the secretion stimulant into the first container R containing the discharged defined amount of the total blood, using the automated suction/discharge device;
    allowing the defined amount of the total blood and secretion stimulant to incubate under nonsterile conditions, forming a mixture, for the secretion of the molecule by the cell either (i) in the first container R or (ii) in a second container S after suctioning and discharge of the mixture using the automated suction/discharge device; and,
    detecting the immune cellular response in the mixture, wherein the detection of the immune cellular response indicates the presence of an immune cellular response specific for the secretion stimulant,
    wherein the automated stimulation and detection method for detecting the immune cellular response is performed under nonsterile conditions.

5. The automated stimulation and detection method of claim 4, wherein the secretion stimulant is a nonspecific stimulant or a stimulant specific for a pathogenic microorganism.

6. The automated stimulation and detection method of claim 4, wherein the secretion stimulant is an antigen highly specific for *Mycobacterium tuberculosis*, which may be absent from the BCG (*Bacillus* Calmette-Guérin) vaccine.

7. The automated stimulation and detection method of claim 6, wherein the secretion stimulant is selected from the group consisting of ESAT-6, CFP-10, and TB7.7 antigens.

8. The automated stimulation and detection method of claim 4, wherein the cell is capable of secreting at least one cytokine.

9. The automated stimulation and detection method of claim 8, wherein the cytokine is selected from the group consisting of interleukins, chemokines, tumor necrosis factor a (TNFα), and interferon gamma (IFNγ).

10. The automated stimulation and detection method of claim 4, wherein the cells are B cells capable of secreting an antibody.

11. The automated stimulation and detection method of claim 4, wherein the total blood is of human, bovine, canine, feline, or equine origin.

12. The automated stimulation and detection method of claim 4, wherein the duration of the incubation is between 2 and 72 h.

13. The automated stimulation and detection method of claim 4, wherein the detection is performed by a sandwich immunoassay.

14. The automated stimulation and detection method of claim 4, wherein the detection is performed by a competition assay using a labeled compound that competes with the immune effector molecule.

15. The automated stimulation and detection method of claim 4, carried out with a single instrument.

16. The automated stimulation and detection method of claim 4, carried out in a single day.

17. The automated stimulation and detection method of claim 4, wherein the incubation and detection are carried out on different days.

18. The automated stimulation and detection method of claim 4, wherein the method is used for the diagnosis of a pathological condition, for a medicament or vaccine toxicity study, or for determining the immune status of a patient based on the secretion stimulant used and the immune effector molecule secreted.

* * * * *